United States Patent
Bae et al.

(10) Patent No.: US 11,103,673 B2
(45) Date of Patent: Aug. 31, 2021

(54) METHOD FOR OPERATING A SLEEP MODE IN A MASSAGE CHAIR USING PROGRESSIVE MUSCULAR RELAXATION AND THE MASSAGE CHAIR CAPABLE OF USING THE SAME

(71) Applicant: Coway Co., Ltd., Chungcheongnam-do (KR)

(72) Inventors: Byoung Chan Bae, Seoul (KR); Yeon Soo Seong, Seoul (KR); Ji Hoon Hyun, Seoul (KR); Sun Young Lee, Seoul (KR); Ju Hyun Baek, Seoul (KR); Joong Keun An, Seoul (KR)

(73) Assignee: Coway Co., Ltd., Chungcheongnam-Do (KR)

(*) Notice: Subject to any disclaimer, the term of this patent is extended or adjusted under 35 U.S.C. 154(b) by 326 days.

(21) Appl. No.: 16/301,059

(22) PCT Filed: Apr. 6, 2017

(86) PCT No.: PCT/KR2017/003762
§ 371 (c)(1),
(2) Date: Nov. 13, 2018

(87) PCT Pub. No.: WO2017/195988
PCT Pub. Date: Nov. 16, 2017

(65) Prior Publication Data
US 2019/0160253 A1    May 30, 2019

(30) Foreign Application Priority Data
May 12, 2016 (KR) .......... 10-2016-0058318

(51) Int. Cl.
*A61M 21/02* (2006.01)
*A61H 15/00* (2006.01)
(Continued)

(52) U.S. Cl.
CPC ............. *A61M 21/02* (2013.01); *A61F 7/08* (2013.01); *A61H 5/00* (2013.01); *A61H 9/00* (2013.01);
(Continued)

(58) Field of Classification Search
CPC ...... A61F 7/08; A61F 9/04; A61F 2007/0004; A61H 5/00; A61H 9/00; A61H 9/0078;
(Continued)

(56) References Cited

U.S. PATENT DOCUMENTS

| 6,592,533 B1* | 7/2003 | Yonekawa | ............... A47C 4/54 601/148 |
| 2002/0183667 A1* | 12/2002 | Kitadou | .................. A47C 3/02 601/91 |

(Continued)

FOREIGN PATENT DOCUMENTS

| CN | 1178667 A | 4/1998 |
| CN | 1270015 A | 10/2000 |

(Continued)

*Primary Examiner* — Tu A Vo
*Assistant Examiner* — Alexander Morales
(74) *Attorney, Agent, or Firm* — Brooks Kushman P.C.

(57) ABSTRACT

A method is provided for operating a sleep mode of a massage chair, which is capable of implementing a sleep mode according to progressive muscle relaxation, and a massage chair for the method is also provided.

10 Claims, 4 Drawing Sheets

(51) Int. Cl.
*A61H 5/00* (2006.01)
*A61H 9/00* (2006.01)
*A61F 7/08* (2006.01)
*A61H 15/02* (2006.01)
*A61F 9/04* (2006.01)
*A61F 7/00* (2006.01)
*A61M 21/00* (2006.01)

(52) U.S. Cl.
CPC .......... *A61H 9/0078* (2013.01); *A61H 15/00* (2013.01); *A61H 15/0078* (2013.01); *A61H 15/02* (2013.01); *A61F 9/04* (2013.01); *A61F 2007/0004* (2013.01); *A61H 2015/0007* (2013.01); *A61H 2201/0149* (2013.01); *A61H 2201/0207* (2013.01); *A61H 2201/1207* (2013.01); *A61H 2201/1409* (2013.01); *A61H 2201/1604* (2013.01); *A61H 2201/1614* (2013.01); *A61H 2201/1623* (2013.01); *A61H 2201/1638* (2013.01); *A61H 2201/1642* (2013.01); *A61H 2201/5046* (2013.01); *A61H 2201/5097* (2013.01); *A61H 2203/0443* (2013.01); *A61H 2205/024* (2013.01); *A61H 2205/04* (2013.01); *A61H 2205/081* (2013.01); *A61H 2205/083* (2013.01); *A61M 2021/0022* (2013.01); *A61M 2021/0066* (2013.01)

(58) Field of Classification Search
CPC .... A61H 15/00; A61H 15/0078; A61H 15/02; A61H 2015/0007; A61H 2201/0149; A61H 2201/0207; A61H 2201/1207; A61H 2201/1409; A61H 2201/1604; A61H 2201/1614; A61H 2201/1623; A61H 2201/1638
See application file for complete search history.

(56) References Cited

U.S. PATENT DOCUMENTS

| | | | | |
|---|---|---|---|---|
| 2007/0213650 | A1* | 9/2007 | Raley | A61H 9/0078 604/4.01 |
| 2008/0048475 | A1* | 2/2008 | Tanizawa | A61H 23/04 297/284.6 |
| 2010/0198121 | A1* | 8/2010 | Tago | A61H 9/0078 601/150 |
| 2011/0055720 | A1* | 3/2011 | Potter | G06F 3/017 715/747 |
| 2012/0144590 | A1* | 6/2012 | Sharp | A47C 7/383 5/639 |
| 2012/0179074 | A1* | 7/2012 | Ikebe | A61H 15/0078 601/19 |
| 2016/0220414 | A1* | 8/2016 | Devine | A61F 7/02 |
| 2017/0035647 | A1* | 2/2017 | Yoshida | A61H 9/0078 |

FOREIGN PATENT DOCUMENTS

| | | |
|---|---|---|
| CN | 101133995 A | 3/2008 |
| CN | 101778612 A | 7/2010 |
| CN | 102665640 A | 9/2012 |
| KR | 100676752 B1 * | 1/2007 |
| KR | 100676752 B1 | 1/2007 |
| KR | 1020110137142 A | 12/2011 |
| KR | 1020120088633 A | 8/2012 |
| KR | 101288406 B1 | 7/2013 |
| KR | 101502117 B1 | 3/2015 |
| KR | 1020150145928 A | 12/2015 |
| KR | 1020160016822 A | 2/2016 |
| KR | 20160046011 A * | 4/2016 |
| KR | 1020160046011 A | 4/2016 |

* cited by examiner

METHOD FOR OPERATING A SLEEP MODE IN A MASSAGE CHAIR USING PROGRESSIVE MUSCULAR RELAXATION AND THE MASSAGE CHAIR CAPABLE OF USING THE SAME

CROSS-REFERENCE TO RELATED APPLICATION

This application is the U.S. national phase of PCT Application No. PCT/KR2017/003762 filed on Apr. 06, 2017, which claims priority to KR Patent Application No. 10-2016-0058318 filed on May 12, 2016, the disclosures of which are incorporated in their entirety by reference herein.

TECHNICAL FIELD

The present disclosure relates to a method for operating a sleep mode of a massage chair, which is capable of implementing a sleep mode according to progressive muscle relaxation, and a massage chair for the method.

BACKGROUND ART

A massage chair is a chair designed to provide a mechanical massage at home or at work without a need for a professional massage therapist. A variety of actuating devices such as airbags, massage balls, and so on are provided in the massage chair so that the user sitting on the massage chair can operate the massage chair to receive the massages including pressing, heating, and so on.

FIG. 1 shows a massage chair according to the related art. The massage chair according to the related art includes a backrest portion 100, a seat portion 200, leg fixing portions 300, a support frame 400, and an operating portion 500.

The backrest portion 100 is configured to support the back of the user and is adjustable to predetermined angles relative to the support frame 400 and the seat portion 200. A headrest 110 is positioned at an upper portion of the backrest portion 100 so that the user's head is placed thereon. The headrest 110 is made of a material that may provide a cushioning feeling.

A pair of shoulder fixing portions 120 are attached to both sides, i.e., to left and right sides of the headrest 110 of the backrest portion 100.

The seat portion 200 is where the hips and the upper thigh of the user are placed and is generally fixed to the support frame 400. It is made of a material that may provide a cushioning feeling.

The leg fixing portions 300 are configured to hold the user's legs, and are provided with a pair of grooves in which the user's calves are inserted. The leg fixing portions 300 are adjustable to a predetermined angle relative to the fixed support frame 400 and the seat portion 200.

The foot fixing portions 310 are attached to lower ends of the leg fixing portions 300. The foot fixing portions 310 are portions on which the user can rest his or her feet and the foot fixing portions 310 hold the feet in place during massaging operation. The foot fixing portions 310 are attached to the leg fixing portions 300 and accordingly, operated together when the leg fixing portions 300 are operated.

The seat frame 400 is attached to the left and right sides of the seat portion 200 to securely hold the massage chair as a whole even during operation of the backrest portion 100 and the leg fixing portion 300, and during operation of the foot fixing portion 310. To this end, a lower frame 450 for fixing the massage chair to the floor is positioned at the lower end of the seat frame 400.

Arm fixing portions 410 are positioned at an upper end of the seat frame 400. The arm fixing portions 410 are portions on which the user can rest his/her arms and they 410 hold the arms in place during massaging operation.

The operating portion 500 is operable by the user and may be configured with a button or a touch panel.

Meanwhile, when the massage chair is used at home, the user receiving massages in the massage chair often falls asleep in the middle of receiving massaging operation in the massage chair, as the user feels relaxation of body. In light of this experience, the user may sit in the massage chair and operate it with the intention of going to sleep from the beginning. In view of this, the massage chair recently provides a dedicated sleep mode.

However, it is easy to fall asleep in the massage chair, but it is rather uncomfortable to keep sleeping for a certain time. This is because the angle between the backrest portion 100 and the leg fixing portion 300 of the massage chair held to perform the massaging operation is not suitable for sleeping (see FIG. 1) and although the back surface in contact with the user's back may provide the cushioning feeling, the user is still not provided with comfortable feeling in the front direction including his/her abdomen, unless the user is covered with a separate blanket. The greatest concern is with the use of various airbags of the massage chair. That is, since airbags are driven with the purpose of providing massages, when the airbags are operated in a state in which the user's muscles are relaxed insufficiently, the airbag can give an excessive pressing, and therefore, the muscles that are not relaxed yet are stimulated by the airbag's pressure even when the user is in sleep.

Accordingly, the present disclosure aims to provide a sleep mode, which allows a user to easily fall asleep, and after the user sleeping, the sleep mode avoids disturbing the user from sleeping until a desired time.

The conventional literature related to the sleep mode will be described below.

Korean Patent Publication No. 2011-0137142 discloses a massage chair that induces sleep activity by stimulating sleep stimulation points. This prior art document is not related to a technique for keeping the user sleeping, but is rather a technique for making the user fall asleep even when the user does not have an intention to sleep ( 수면 의자가 없는 -> 수면 의지가 없는 ?). Further, there is a problem that, since different users have different sleep stimulation points, it cannot be considered that the sleep induction is generally performed, and rather, the users can be sometimes awoken from sleeping depending on the stimulation points.

Korean Patent No. 10-1288406 discloses a massage chair provided with a helmet capable of supporting the head and the neck so as to induce sound sleep, but the need to wear the helmet rather bothers the user who wants to relax in the massage chair, and the presence of the helmet instead prevents the user from easily going into sleep, or even worse, awakens the user if the user falls asleep during the massage.

PRIOR ART DOCUMENT

Patent Documents (Patent Document 1) KR 10-2011-0137142A
(Patent Document 2) KR 10-1288406B (Patent Document 3) KR 10-1502117B
(Patent Document 4) KR 10-2012-0088633A

DISCLOSURE

Technical Problem

The present disclosure is designed to solve the problems described above.

More specifically, the present disclosure provides a method for operating the sleeping mode of a massage chair, which can allow users to easily get into sleeping state, and after the user is in sleep, keep the user in the sleeping state for a desired time without disturbing the user.

For this purpose, the present disclosure is designed to provide a method for operating a sleeping mode of a massage chair, which applies progressive muscular relaxation to provide comfortable relaxation of the muscles so that user can easily fall asleep, and also relaxes the muscles sufficiently even after the user is asleep so that the muscles are not agitated by the massaging operation of the massage chair.

In addition, the present disclosure is designed to provide a method for operating a sleep mode of a massage chair, which can provide an environment similar to an actual sleeping environment to help a user to have a sound sleep.

Technical Solution

In an embodiment of the present disclosure provided to solve the problems mentioned above, a method for operating a sleep mode of a massage chair is provided, in which the massage chair may include: a seat portion 200 having a massage ball assembly 600 provided therein; a backrest portion 100 which is pivotable with one side thereof being fixed to the seat portion 200, and including shoulder fixing portions 120 provided on both left and right sides; leg fixing portions 300 which are pivotable with one side thereof being fixed to the seat portion 200; a support frame 400 which fixes the seat portion 200 and includes arm fixing portions 410 positioned therein; and an operating portion 500, in which the method may include steps of: (a) applying a sleep massage signal through the operating portion 500; (b) sensing a neck position and moving the massage ball assembly 600 to a height of the neck position and operating the same; (c) actuating shoulder airbags 129 within the shoulder fixing portions 120; (d) actuating arm airbags 419 in the arm fixing portions 410; (e) pivoting the backrest portion 100 and the leg fixing portions 300 to a predetermined sleep angle; (f) lowering and operating the massage ball assembly 600 from a back position; (g) actuating and releasing pelvic airbags 209 in the seat portion 200 and leg airbags 309 in the leg fixing portions 300; (h) releasing the arm airbags 419; and (i) releasing the shoulder airbags 129.

Further, at the step (a), a sleep massage signal is inputted through the operating portion 500 together with a sleep massage time, and after the step (i), the method may preferably further include a step (j) of pivoting the backrest portion 100 and the leg fixing portions 300 to a predetermined maximum angle after the sleep massage time elapses.

Further, when the sleep massage time is not inputted to the operating portion 500 at the step (a), a predetermined sleep massage automatic set time is preferably set as the sleep massage time at the step (j).

Further, after the step (j), the method preferably further includes a step (k) of activating the shoulder airbags 129, the pelvic airbags 209, the leg airbags 309, and the arm airbags 419.

Further, after the step (a) and before the step (b), the method preferably further includes a step of applying an operating signal to a thermal eye patch 131 through the operating portion 500 and operating the thermal eye patch 131.

Further, after the step (a), the method preferably further includes a step of applying an operating signal to a thermal abdominal pad 231 through the operating portion 500 and operating the thermal abdominal pad 231.

Further, the arm airbags 419 preferably include a right arm airbag and a left arm airbag, and the step (d) is preferably a step of actuating the right arm airbag and then the left arm airbag.

Further, it is preferable that the pelvic airbags 209 include a right pelvic airbag and a left pelvic airbag, and the leg airbags 309 include a right leg airbag and a left leg airbag, and the step (g) is a step of activating the right pelvic airbag, then the right leg airbag, then the left pelvic airbag, then the left leg airbag, and then releasing all the left and right leg airbags 309 are released, and then releasing all the left and right pelvic airbags 209.

It is preferable that a back airbag 109 is further provided within the seat portion 200, and after the step (i), the method further includes a step of actuating and then releasing the back airbag 109.

In another embodiment of the present disclosure for solving the above problem, a massage chair capable of driving the method for operating a sleep mode of a massage chair described above is provided, in which a headrest 110 is provided on an upper side of the backrest portion 100, and a thermal eye patch pocket 130 is positioned within the headrest 110 to receive the thermal eye patch 131 to be inserted therein.

Further, the massage chair preferably includes a thermal abdominal pad pocket 230 positioned on the support frame 400 or the seat portion 200 to receive the thermal abdominal pad 231 to be inserted therein.

Further, the massage chair preferably includes hand fixing portions 411 inclined downward from the arm fixing portions 410 are positioned at one ends of the arm fixing portions 410.

Effects of the Invention

The present disclosure enables implementation of progressive muscular relaxation in a massage chair. Since the user's muscles are progressively relaxed, the user can easily fall asleep while receiving massages in the massage chair. In addition, since the user receives the massaging operation with the muscles in the relaxed state, the muscles are less likely to be tensed by the action of the airbag and the like, so that the user can keep in the sleeping state sufficiently for a desired time.

In addition, use of a thermal eye patch and a thermal abdominal pad can allow a user to feel the comfort of sleeping similar to actual sleeping in a bed, so that the user can take a sound sleep for a desired time.

In addition, the massage chair can smoothly and naturally wake up the user after the desired sleeping time has elapsed.

In addition, since the relatively large size of the massage chair can be attributable to the arm fixing portion, the overall size of the massage chair can be reduced to some extent by changes in the shape of the arm fixing portion. The size of massage chair generally limits its placement to where the massage chair can be installed, and the massage chair in a reduced size has a considerable advantage in view of installation position.

DETAILED DESCRIPTION

Figure 1:
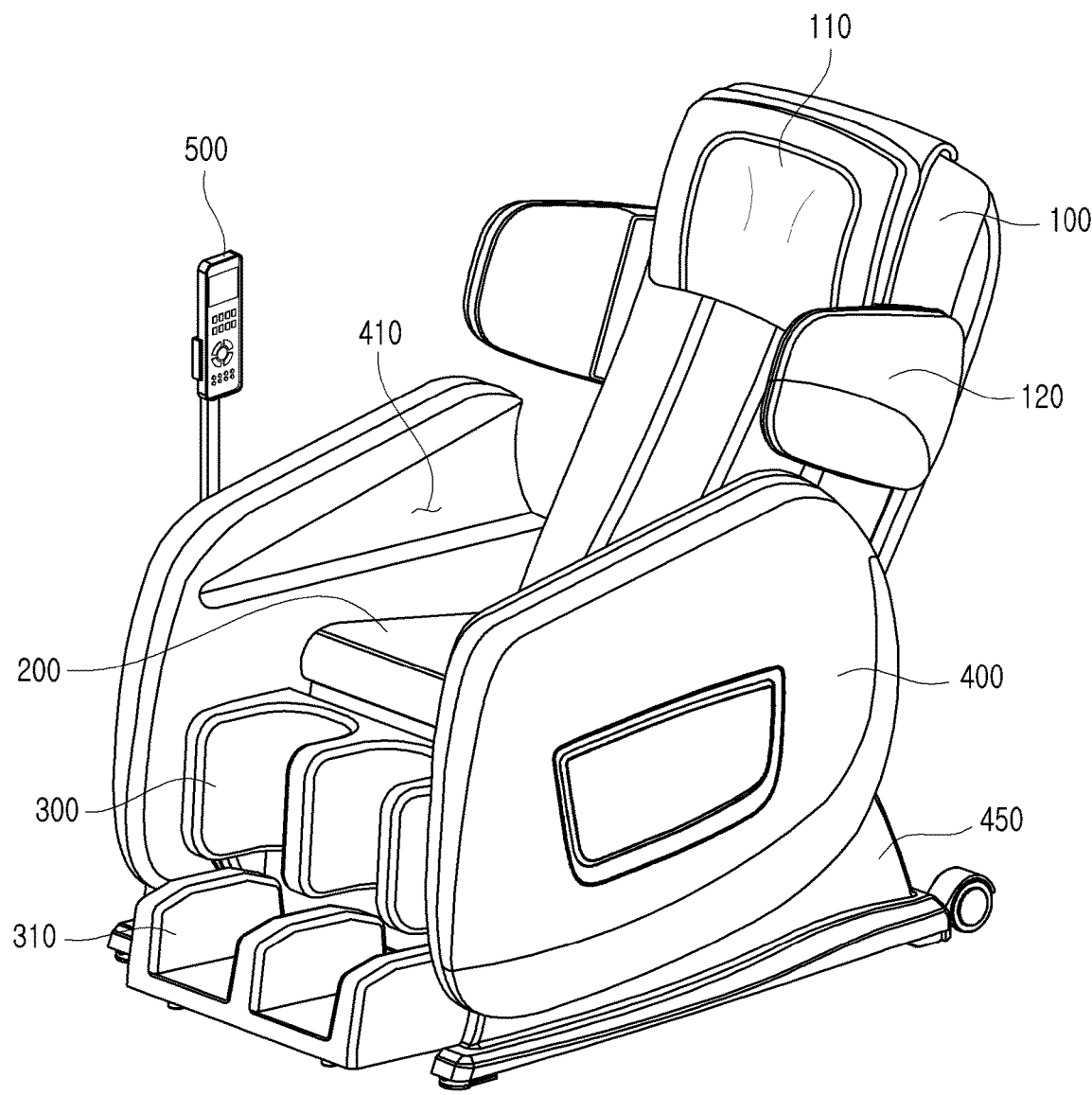
FIG. 1 is a perspective view of a massage chair according to the related art.

Hereinafter, the present disclosure will be described in detail with reference to the drawings.

In the following drawings, based on an assumption that the user is seated in the massage chair, "upper" and "lower" sides refer to upward and downward directions of the user, and "front" side refers to a "forward" direction where the user sees, and "back" side refers to a "backward" direction of the user.

The backrest portion 100, the leg fixing portion 300, and the foot fixing portion 310, which will be described later, are capable of rotating motion or upward and downward motions, respectively, and for this purpose, a separate actuator (not illustrated) is provided, which will not be described in detail about the operation principle since it is already well known.

In addition, the operation principle involved with the mode selection, change, and operation of the massage chair by the operating portion 500, which will be described later, in accordance with a signal applied to the operating portion 500 is transmitted to a controller portion (not illustrated), also will not be described in detail, since it is already well known in the art.

Description of Massage Chair

The massage chair implementing a method according to the present disclosure will be described with reference to FIGS. 2 and 3. The like or same components as those of the massage chair according to the related art shown in FIG. 1 will not be redundantly described.

The massage chair includes a backrest portion 100, a seat portion 200, leg fixing portions 300, a support frame 400, and an operating portion 500.

The backrest portion 100 is provided with a headrest 110 having a cushioning material so that the user can rest his head on the headrest 110. Unlike the related art, a thermal eye patch pocket 130 is positioned in the headrest 110.

A thermal eye patch 131 may be kept inside the thermal eye patch pocket 130. The user may remove the thermal eye patch 131 from the thermal eye patch pocket 130 and wear it around his/her eyes during an operation of the massage chair.

The thermal eye patch 131 may be connected to the massage chair by wires or wirelessly, and the user may control the operation by applying an operation signal through the operating portion 500. For example, when the user operates the thermal eye patch 131 through the operating portion 500, the thermal eye patch 131 is heated by a built-in power source or by power supply received from the massage chair to provide the user with a thermal sensation.

A movable massage ball assembly 600 is mounted at the center of the backrest portion 100.

The massage ball assembly 600 has a structure that includes a plurality of balls, and is vertically or horizontally movable within the backrest portion 100 along a predetermined orbit. During the massaging operation, the massage ball assembly 600 is moved within the backrest portion 100 along a predetermined orbit, with a plurality of balls moving and pressing along the user's back or shoulders, thus providing massages. In another embodiment, the massage ball assembly 600 itself may be heated to provide additional thermal sensation to the user.

A back airbag 109 is positioned within the backrest portion 100. One back airbag 109 may be provided at the center, or two or more airbags 109 may be provided in a left-right direction.

Shoulder fixing portions 120 are positioned on both sides, i.e., on left and right sides of the backrest portion 100 and shoulder airbags 129 are positioned on the shoulder fixing portions 120, respectively.

The seat portion 200 is fixed to the support frame 400. Pelvic airbags 209 are positioned on both sides of the seat portion 200, and between the seat portion 200 and the support frame 400 in an inner direction toward the user. The pelvic airbags 209 may also press the back of the user in which case the pelvic airbag 209 may also be referred to as a waist airbag.

A thermal abdominal pad pocket 230 is positioned on the seat portion 200 or the support frame 400, or between the seat portion 200 and the support frame 400. A thermal abdominal pad 231 may be stored inside the thermal abdominal pad pocket 230. The user may remove the thermal abdominal pad 231 from the thermal abdominal pad pocket 230 and then cover his/her abdomen with the same during operation of the massage chair.

The thermal abdominal pad 231 may be connected to the massage chair by wires or wirelessly, and the user may control the operation by applying an operation signal through the operating portion 500. For example, when the user operates the thermal abdominal pad 231 through the operating portion 500, the thermal abdominal pad 231 is heated by a built-in power source or by power supply received from the massage chair to provide the user with a thermal sensation.

The leg fixing portions 300 are configured to hold the user's legs and provided with a pair of grooves in which the user's calves are inserted. The leg airbags 309 are positioned inside the grooves.

One leg airbag 309 may include a pair of right and left airbags or each of the pair of right and left airbags may include a pair of upper and lower airbags, in which case one leg airbag 309 includes a total of four airbags.

Foot fixing portions 310 are positioned at the lower ends of the leg fixing portions 300.

The foot fixing portions 310 may be integrally formed with the leg fixing portions 300, or the foot fixing portion 310 may be relatively movable up and down with respect to the leg fixing portions 300 to suitably fit the body size (i.e., length of legs or calves) of the user.

Foot airbags 319 are positioned in the grooves of the foot fixing portion 310. One foot airbag 319 may include a pair of right and left airbags or each of the pair of right and left airbags may include a pair of upper and lower airbags, as shown in FIG. 3, in which case one foot airbag 310 includes a total of four airbags.

The seat frame 400 is positioned to the left and right sides of the seat portion 200 to securely hold the massage chair as a whole even during operation of the backrest portion 100 and the leg fixing portions 300, and during operation of the foot fixing portions 310. To this end, a lower frame 450 for fixing the massage chair to the floor is positioned at the lower end of the seat frame 400.

Arm fixing portions 410 are positioned at an upper end of the seat frame 400. The arm fixing portions 410 are portions on which the user can rest his/her arms and they 410 fix the arms in place during massaging operation.

Arm airbags 419 are positioned within the arm fixing portions 410. One arm airbag 419 may include a pair of upper and lower airbags, respectively, or each of the pair of upper and lower airbags may include a pair of left and right airbags, in which case one arm airbag 410 includes a total of four airbags.

The arm fixing portions 410 according to the related art are protruded from a front of the massage chair as they are formed in consideration of a situation where the user stretches out his/her arms to full length, as shown in FIG. 1. In this case, the seat frame 400 provided with the arm fixing portions 410 is protruded together, resulting in increased size of the massage chair and limited installation position.

Figure 2:
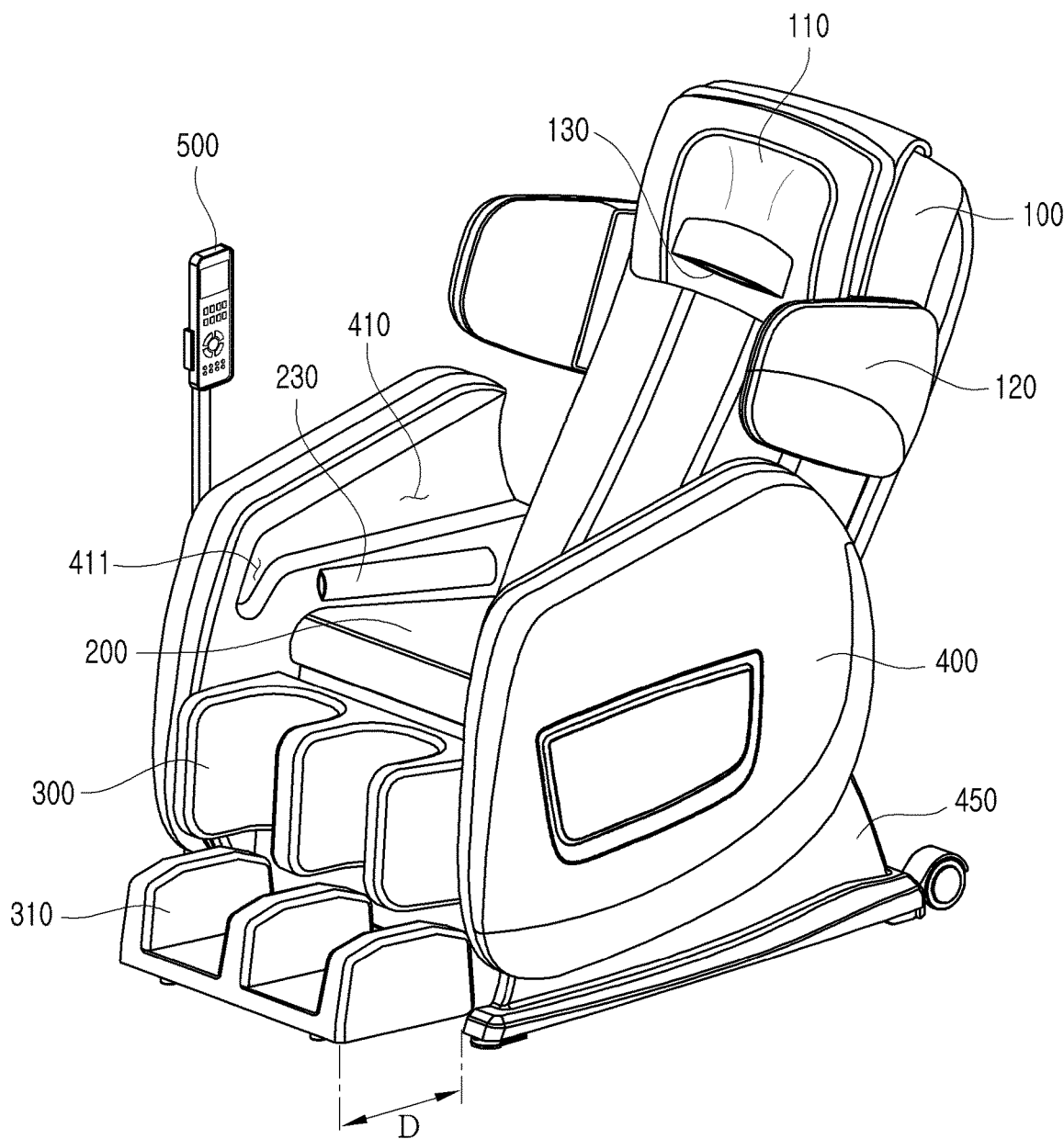
FIG. 2 is a perspective view of a massage chair according to the present disclosure.
Figure 3:
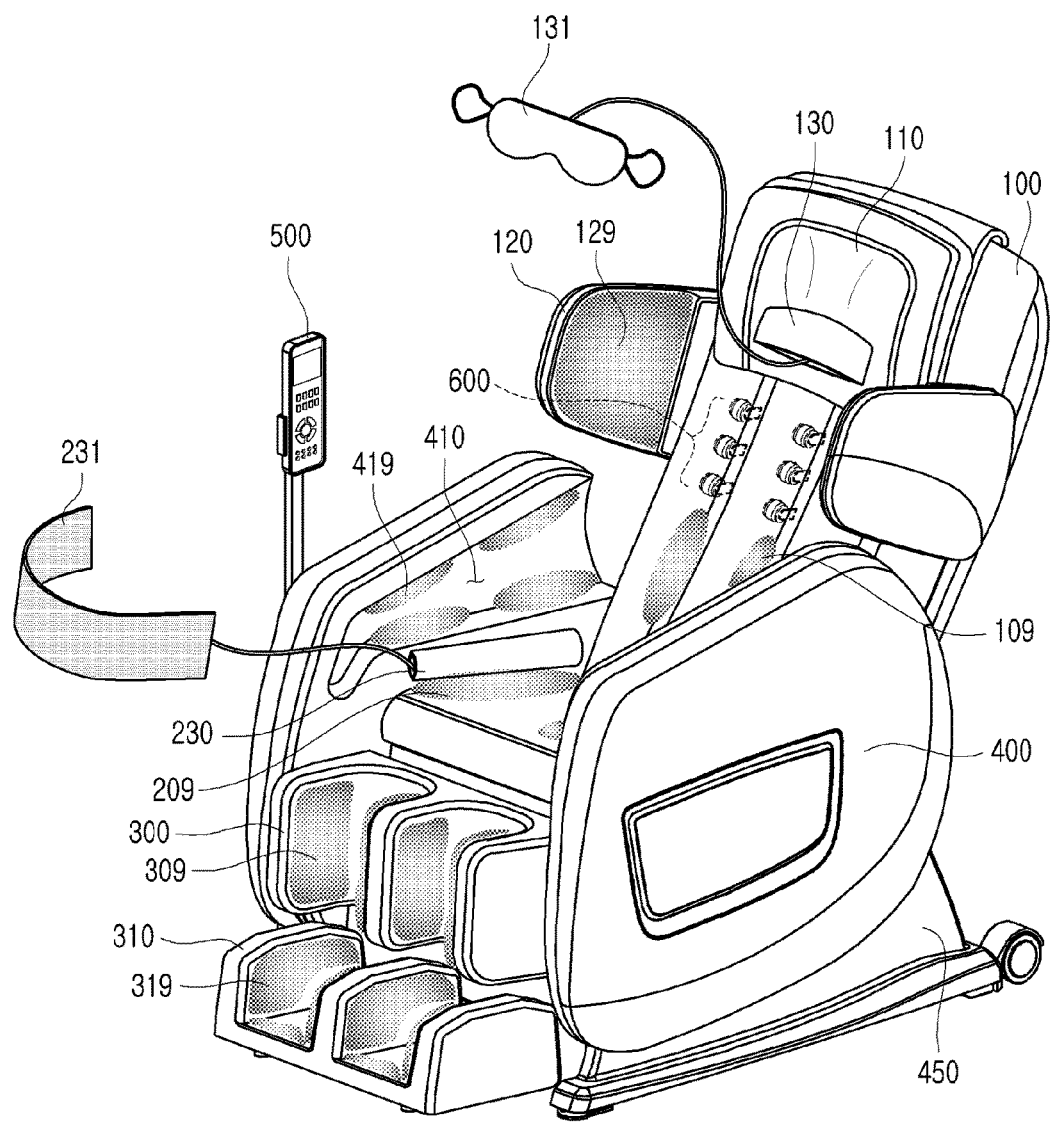
FIG. 3 is a perspective view illustrating an airbag of a massage chair according to the present disclosure.
Figure 4:
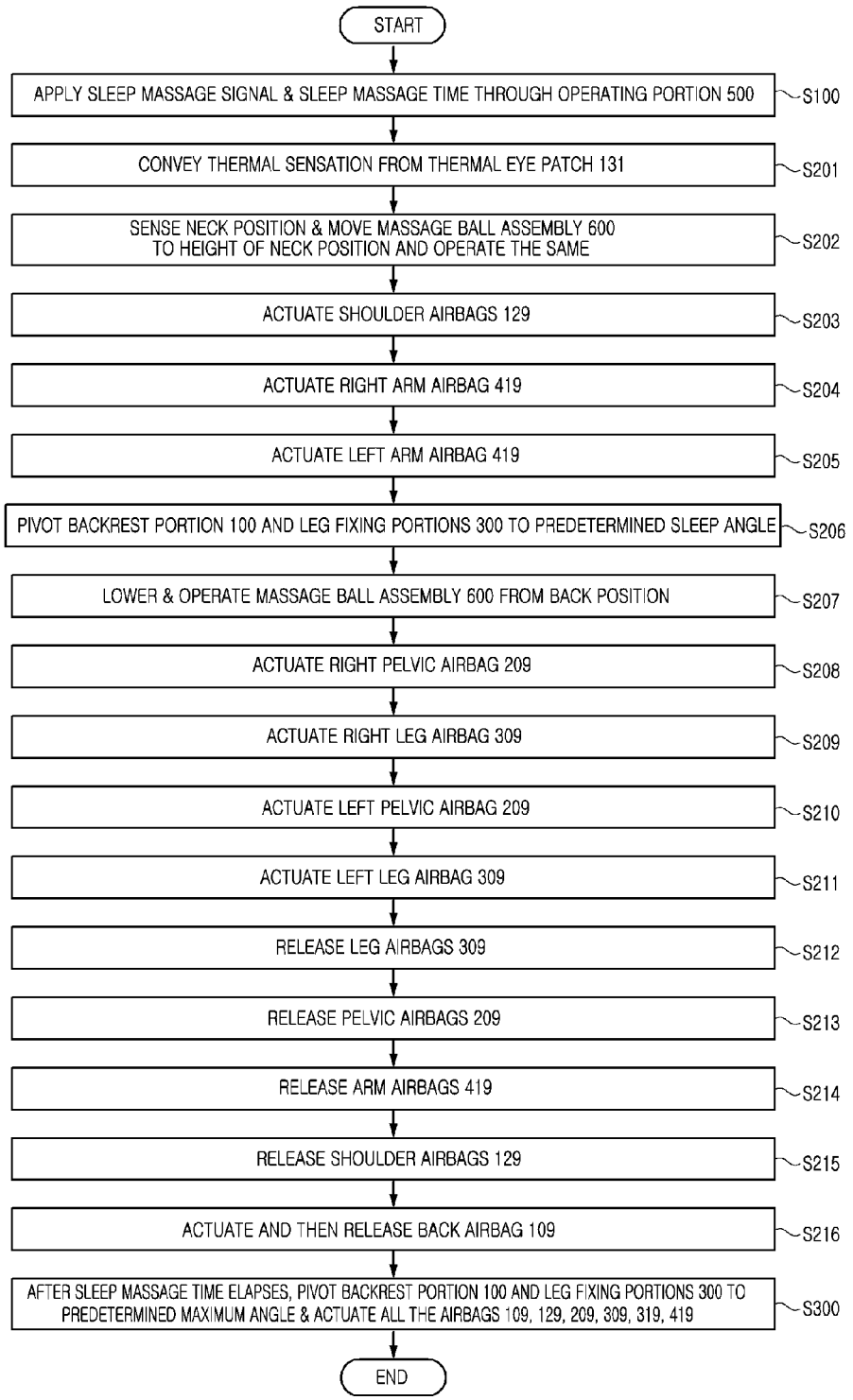
FIG. 4 is a flowchart provided to explain a sleep mode of a massage chair according to the present disclosure.

As shown in FIG. 2, the hand fixing portions 411 which are inclined downward, are positioned at one end of each of the arm fixing portions 410 according to the present disclosure. In this way, the substantial length of the arm fixing portions 410 can be reduced (D), which means a reduction in the overall size of the seat frame 400, thereby reducing the overall size of the massage chair and at the same time, reducing restriction of the installation positions.

The operating portion 500 is operable by the user, and may be configured with a button or a touch panel. The operating portion 500 may be generally provided on the right side of the massage chair to facilitate operating on the operating portion 500 with a right hand, although it 500 may be provided on the left side depending on needs.

It is preferable that the operating portion 500 and the massage chair are connected to each other by a material that is rigid but is deformable to certain extent. A cable may be mounted inside the operating portion 500, connecting the operating portion 500 with a controller (not illustrated) within the massage chair.

The user may select various modes through the operating portion 500 to apply corresponding signals to a controller portion (not illustrated), and accordingly, the operating portion 500 may transmit the signals corresponding to the selected mode to the controller portion (not illustrated) to operate an actuator (not illustrated) or the like to operate the backrest portion 100, the leg fixing portions 300 and the foot fixing portions 310 to change angles thereof or to control the operation of the massage ball assembly 600 and various airbags 109, 129, 209, 309, 319 and 419, or to control the thermal eye patch 131 and the thermal abdominal pad 231 described above.

Description of Sleep Mode of Massage Chair

Before operating the sleep mode, the user may preferably remove the thermal eye patch 131 from the thermal eye patch pocket 130 and wear the same, and remove the thermal abdominal pad 231 from the thermal abdominal pad pocket 230 to cover his/her abdomen with the same.

At S100, a sleep massage signal and a sleep massage time are applied to the massage chair through the operating portion 500. In some examples, the sleep massage time may not be applied, in which case a predetermined sleep massage automatic set time is set as the sleep massage time.

The massage chair now emulates the progressive muscular relaxation, thus providing massaging motions of the massage chair, at S201 to S216.

First, the thermal eye patch 131 is operated to convey the thermal sensation around the eyes of the user, at S201. In another embodiment, the thermal abdominal pad 231 may operate to further convey the thermal sensation to the abdomen.

Next, the massage chair senses the neck position, and the massage ball assembly 600 moves to the height of the neck position to start the neck massage, at S202.

Next, the shoulder airbags 129 within the shoulder fixing portions 120 are actuated, at S203.

Next, the arm airbags 419 within the arm fixing portions 410 are actuated, and preferably actuated one by one for progressive muscle relaxation. That is, it is preferable that the right arm airbag is actuated first at S204, followed by the actuation of the left arm airbag at S205.

Next, the backrest portion 100 and the leg fixing portions 300 are pivoted to a predetermined sleep angle, at S206. In an example, the sleep angle may be an angle close to 180 degrees. That is, the leg fixing portions 300 may be raised and the backrest portion 100 may be reclined so that the user can have entire body relaxed as if he/she is lying on a real bed.

In this state, the massage ball assembly 600 is lowered and actuated from the back position to a direction of the pelvis, at S207.

Next, the pelvic airbags 209 and the leg airbags 309 in the leg fixing portions 300 are actuated and released. In this example, while the airbags in the left and right sides are separately actuated, it is also preferable for progressive muscle relaxation that the airbags are actuated in the order of the pelvis and the leg on one side, and the pelvis and the leg on the other side. That is, the right pelvic airbag is actuated at S208, then the right leg airbag is actuated at S209, then the left pelvic airbag is actuated at S210, then the left leg airbag is actuated at S211, and then all the left and right leg airbags 309 are released at S212, and then all the left and right pelvic airbag 209 are released at S213.

Next, the arm airbags 419, which have been in operation from S204 and S205, are released at S214, and the shoulder airbags 129, which have been in operation from S203, are released at S215.

The user's muscular relaxation according to the progressive muscular relaxation is then completed, upon actuation and release of the back airbag 109 at S216.

The user now has relaxed muscles throughout the body according to the progressive muscular relaxation, and with the backrest portion 100 and the leg fixing portions 300 that have been pivoted to the sleep angle and maintained at that angle since S206, the user is now lying comfortably, and there is no airbag in operation. Accordingly, the user may have a good sleep for a desired time (i.e., sleep massage time as applied).

When the sleep massage time elapses, the user is smoothly woken up.

To this end, the backrest portion 100 and the leg fixing portions 300 are pivoted to a predetermined maximum angle upon elapse of the sleep massage time. In an example, the maximum angle is preferably greater than the sleep angle at S206. This allows the user to naturally feel like he/she is stretching after a sound sleep. Simultaneously, all the airbags 109, 129, 209, 309, 319 and 419 are operated at low pressure at S300. This allows the user to sense the suitable pressure to wake up from the sleep.

Although embodiments have been described in accordance with the present invention above for better understanding of those skilled in the art, it will be understood by those skilled in the art that various changes in form and details may be made therein without departing from the spirit and scope of the disclosure as defined by the appended claims.

DESCRIPTION OF REFERENCE NUMERALS

100: backrest portion
109: back airbag
110: Headrest
120: shoulder fixing portion
129: shoulder airbag
130: thermal eye patch pocket
131: thermal eye patch
200: seat portion
209: pelvic airbag
230: thermal abdominal pad pocket
231: thermal abdominal pad
300: leg fixing portion
309: leg airbag
310: foot fixing portion
319: foot airbag
400: support frame
410: arm fixing portion
411: hand fixing portion
419: arm airbag
450: lower frame
500: operating portion
600: massage ball assembly

The invention claimed is:

1. A method for operating a sleep mode of a massage chair comprising:
   a seat portion;
   a backrest portion being pivotally fixed to one side of the seat portion and including shoulder fixing portions on both left and right sides;
   leg fixing portions being pivotally fixed to one side of the seat portion;
   a support frame holding the seat portion and including arm fixing portions positioned therein;
   an operating user interface, a user applies a predetermined instruction via the operating user interface, the operating user interface transmitting a signal corresponding to the predetermined instruction to a controller; and
   a massage ball assembly comprising a plurality of balls and movable within the backrest portion along a predetermined orbit;
   wherein the method comprises sequential steps of:
   (a) applying a sleep massage signal together with a sleep massage time to the massage chair through the operating user interface;
   (b) in response to the sleep massage signal and the sleep massage time being inputted to the operating user interface, moving the massage ball assembly to a height of a neck position and operating the massage ball assembly;
   (c) actuating shoulder airbags within the shoulder fixing portions;
   (d) actuating arm airbags in the arm fixing portions;
   (e) pivoting the massage chair to a predetermined sleep angle, in which the backrest portion is reclined and the leg fixing portions are raised;
   (f) operating the massage ball assembly from a back position towards a pelvis of the user;
   (g) actuating pelvic airbags in the seat portion;
   (h) actuating the leg airbags in the leg fixing portions;
   (i) releasing the leg airbags;
   (j) releasing the pelvic airbags;
   (k) releasing the arm airbags;
   (l) releasing the shoulder airbags;
   (m) actuating and releasing a back airbag which is provided inside the backrest portion;
   (n) stopping the operation of the back airbag, the shoulder airbags, the pelvic airbags, the leg airbags, and the arm airbags, before initiating the sleep massage time;
   (o) pivoting the massage chair to a predetermined maximum angle greater than the predetermined sleep angle after the sleep massage time elapses when the sleep massage time is inputted at the step (a), in which the backrest portion is reclined and the leg fixing portions are raised; and
   (p) actuating the back airbag, the shoulder airbags, the pelvic airbags, the leg airbags, and the arm airbags.

2. The method according to claim 1, wherein, after the step (a), and before the step (b), further comprising a step of applying an operating signal to a thermal eye patch through the operating user interface and operating the thermal eye patch.

3. The method according to claim 2, wherein, after the step (a), further comprising a step of applying an operating signal to a thermal abdominal pad through the operating user interface and operating the thermal abdominal pad.

4. A massage chair capable of driving the method for operating a sleep mode of a massage chair according to claim 3, wherein a headrest is provided on an upper side of the backrest portion,
   and a thermal eye patch pocket is positioned within the headrest to receive the thermal eye patch to be inserted therein.

5. The massage chair according to claim 4, comprising a thermal abdominal pad pocket is positioned on the support frame or the seat portion to receive the thermal abdominal pad to be inserted therein.

6. The massage chair according to claim 4, wherein hand fixing portions inclined downward from the arm fixing portions are positioned at an end of the arm fixing portions.

7. The method according to claim 1, wherein the arm airbags comprise a right arm airbag and a left arm airbag,
   and the step (d) comprises actuating the right arm airbag and then the left arm airbag.

8. The method according to claim 1, wherein the pelvic airbags comprise a right pelvic airbag and a left pelvic airbag, and the leg airbags comprise a right leg airbag and a left leg airbag,
   wherein the step (g) comprises a step of actuating the right pelvic airbag, then the right leg airbag, then the left pelvic airbag, then the left leg airbag;
   wherein the step (h) comprises a step of releasing all of the left and right leg airbags; and
   wherein the step (i) comprises a step of releasing all of the left and right pelvic airbags.

9. The method according to claim 1, wherein at the step (p), the back airbag, the shoulder airbags, the pelvic airbags, the leg airbags, and the arm airbags are operated simultaneously to provide a pressure to wake up a user.

10. The method of claim 1, wherein the steps (a) through (p) cooperate to provide a single complete sleep cycle via massage, sleep, and wake-up.

* * * * *